(12) United States Patent  
Greenberg

(10) Patent No.: US 8,747,455 B2  
(45) Date of Patent: Jun. 10, 2014

(54) BRANCHED STENT GRAFT SYSTEM

(75) Inventor: Roy K. Greenberg, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1027 days.

(21) Appl. No.: 12/188,305

(22) Filed: Aug. 8, 2008

(65) Prior Publication Data

US 2009/0048663 A1 Feb. 19, 2009

Related U.S. Application Data

(60) Provisional application No. 60/963,971, filed on Aug. 8, 2007.

(51) Int. Cl.
*A61F 2/06* (2013.01)
(52) U.S. Cl.
USPC ........................................................ 623/1.35
(58) Field of Classification Search
USPC ................................. 606/108; 623/1.12, 1.35
See application file for complete search history.

(56) References Cited

U.S. PATENT DOCUMENTS

| 6,692,483 B2 | 2/2004 | Vardi et al. ..................... 604/529 |
| 2004/0230287 A1 | 11/2004 | Hartley et al. ............... 623/1.12 |
| 2006/0184228 A1 | 8/2006 | Khoury ........................ 623/1.13 |

FOREIGN PATENT DOCUMENTS

| WO | WO 03/082153 | 10/2003 | ................ A61F 2/06 |
| WO | WO 2005/027784 | 3/2005 | |
| WO | WO 2005/032340 | 4/2005 | |
| WO | WO 2006/041505 | 4/2006 | ................ A61F 2/24 |
| WO | WO 2007/028112 | 3/2007 | ................ A61F 2/06 |

*Primary Examiner* — Thomas J Sweet
*Assistant Examiner* — Matthew Schall
(74) *Attorney, Agent, or Firm* — Brinks Gilson & Lione

(57) ABSTRACT

An endovascular prosthetic system comprising an prosthetic device with a major lumen extending therethrough, a major wall, at least one opening in the major wall; at least one branch extending into the major lumen of the prosthetic device having a minor lumen, a minor wall, and a fenestration in the minor wall in communication with the major lumen; and at least one guide wire extending through the fenestration and out of the prosthesis through the opening.

20 Claims, 10 Drawing Sheets

BRANCHED STENT GRAFT SYSTEM

CROSS-REFERENCE TO RELATED APPLICATION

This application claims the benefit of U.S. Provisional Application No. 60/963,971, filed Aug. 8, 2007, which is incorporated by reference in its entirety.

TECHNICAL FIELD

This invention relates to a prosthetic system for implantation within a human or animal body for the repair of damaged vessels, ducts, or other physiological passageways.

BACKGROUND

Throughout this specification, when discussing the application of this invention to the aorta or other blood vessels, the term "distal", with respect to a prosthesis, is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. In Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurismal, or ruptured vessels involves the use of a prosthetic device to provide some or all of the functionality of the original, healthy vessel, and/or preserve any remaining vascular integrity by replacing a length of the existing vessel wall that spans the site of vessel failure.

It is preferable that these prostheses seal off the failed portion of the vessel. For weakened or aneurysmal vessels, even a small leak in the prosthesis may lead to the pressurization of, or flow in, the treated vessel which aggravates the condition the prosthesis was intended to treat. A prosthesis of this type can, for example, treat aneurysms of the abdominal aortic, iliac, or branch vessels such as the renal arteries.

A prosthetic device can be of a unitary construction or be comprised of multiple prosthetic modules. A modular prosthesis allows a surgeon to accommodate a wide variation in vessel morphology while reducing the necessary inventory of differently sized prostheses. For example, aortas vary in length, diameter, and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Modular systems are typically assembled in situ by overlapping the tubular ends of the prosthetic modules so that the end of one module sits partially inside the other module, preferably forming circumferential apposition through the overlap region. This attachment process is called "tromboning." The connections between prosthetic modules are typically maintained by the friction forces at the overlap region and enhanced by the radial force exerted by the internal prosthetic module on the external prosthetic modules where the two overlap. The fit may be further enhanced by stents fixed to the modules at the overlap region.

A length of a vessel which may be treated by these prostheses may have one or more branch vessels, i.e. vessels anastomosed to the main vessel. The celiac, superior mesenteric, left common carotid, and renal arteries, for example, are branch vessels of the aorta; the hypogastric artery is a branch vessel of the common iliac artery. If these branch vessels are blocked by the prosthesis, the original blood circulation is impeded and the patient can suffer. If, for example, the celiac artery is blocked by the prosthesis, the patient can experience abdominal pain, weight loss, nausea, bloating, and loose stools associated with mesenteric ischemia. The blockage of any branch vessel is usually associated with unpleasant or even life-threatening symptoms.

When treating a vessel with a prosthetic device, it is therefore preferable to preserve the original circulation by providing a prosthetic branch that extends from the prosthesis to a branch vessel so that the blood flow into the branch vessel is not impeded. For example, the aortic section of the ZENITH® abdominal aortic prosthesis (Cook, Inc., Bloomington, Ind.), described below, can be designed to extend above the renal arteries and to have prosthetic branches that extend into the renal arteries. Alternatively, the iliac branches of the ZENITH® device can be designed to extend into the corresponding hypogastric arteries. Branch extension prosthetic modules ("branch extensions") can form a tromboning connection to the prosthetic branch to complete the prosthesis. Furthermore, some aneurysms extend into the branch vessels. Deploying prosthetic branches and branch extensions into these vessels may help prevent expansion and/or rupture of these aneurysms. High morbidity and mortality rates are associated with these aneurysms.

Aortic arch stent grafts are used in treating dissection and aneurismal dilation of the aortic arch. Many of these grafts have branches that maintain the patency of the branch arteries originating in the arch (the innominate, left common carotid, and left subclavian arteries) and help direct the flow of blood into the branch arteries. Many of these branched grafts have branches that project outward from the prosthesis. Implanting the stent grafts in the branch arteries provides a challenge to surgeons because of the anatomic features of the aortic arch. Blood flow from the branch arteries must not be interrupted for an extending length of time because they supply blood to the brain. Implanting branch stents that mate with the branches presents challenges because the natural orientation of the aortic arch must be matched or simulated by the stent grafts.

A surgeon may access the aortic arch through the branch arteries to implant small vessel stents. Guide wires are used to link the small vessel stents in the branch arteries with the branches of the aortic arch stent. However, much time may be lost in threading the guide wires through the openings of the aortic arch stent branches and through the branch arteries. A surgeon will often manipulate the guide wire around the difficult angles in the aortic arch stent channels before being able to connect with the delivery catheter of the branched stent.

BRIEF SUMMARY

The present invention provides an endovascular prosthetic device for implantation in an aortic arch. The endovascular prosthetic device comprises a primary prosthesis comprising a major lumen and at least one socket for receiving a secondary prosthesis. The secondary prosthesis is to be deployed in a branch artery. The at least one socket has at least a portion that extends into the major lumen and is configured or angled in a proximal direction to direct blood flowing from the heart to a branch artery. The at least one socket has a fenestration in its wall to accommodate a guide wire. The guide wire passes through the major lumen from a distal location into the at least one socket through the fenestration to facilitate placement of the secondary prosthesis in the branch artery. On some embodiments there is at least one fenestration in the wall of the socket.

In another aspect of the invention, there is an endovascular system for implantation in an aortic arch. The system comprises an endovascular prosthetic device, as described above, and includes the secondary prosthesis for implantation in a branch artery. The secondary prosthesis can be small vessel prosthetic grafts, such as stent grafts.

In yet another aspect of the invention, there is an endovascular prosthetic device comprising a prosthetic device with first and second sockets, and one guide wire extending through the fenestration in the first socket and then through the fenestration in the second socket.

Another aspect of the invention provides an endoluminal prosthetic device having three sockets. Each socket has at least one fenestration through which a guide wire extends. In some embodiments, there are three guide wires, one for each socket. In other embodiments, there is one guide wire extending through the fenestrations in each socket. The sockets in the prosthetic device correspond to the innominate, left common carotid, and left subclavian arteries that branch from the aortic arch.

DETAILED DESCRIPTION OF THE DRAWINGS AND THE PRESENTLY PREFERRED EMBODIMENTS

Figure 1A:
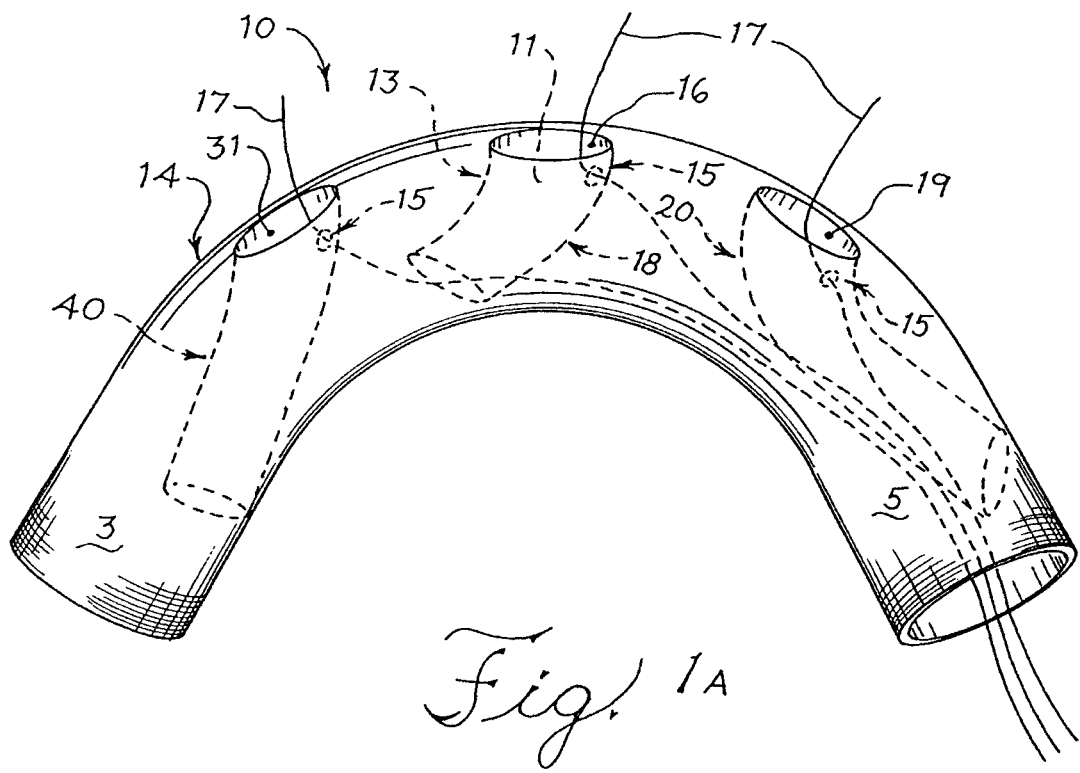
FIG. 1A illustrates a prosthetic device with two sockets and two guide wires extending through the sockets and holes into the major lumen.

The term "endoluminal" describes objects that are found or can be placed inside a lumen in the human or animal body. The term "endovascular" describes objects that are within a blood vessel. A lumen can be an existing lumen or a lumen created by surgical intervention. This includes lumens such as blood vessels, parts of the gastrointestinal tract, ducts such as bile ducts, parts of the respiratory system, etc. A "prosthetic device" is thus a prosthesis that can be placed inside one of these lumens.

The term "stent" means any device or structure that adds rigidity, expansion force, or support to a prosthesis. A Z-stent is a stent that has alternating struts and peaks (i.e., bends) and defines a generally cylindrical lumen. The "amplitude" of a Z-stent is the distance between two bends connected by a single strut. The "period" of a Z-stent is the total number of bends in the Z-stent divided by two, or the total number of struts divided by two.

The term "endoleak" refers to a leak around or through a prosthetic device. Endoleaks can occur through the fabric of a prosthesis, through the interconnections of a modular prosthesis, or around the ends of the prosthesis, inter alia. Endoleakage may result in the repressurizing of an aneurysm.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

The term "prosthetic branch" refers to a portion of a prosthesis that is anastomosed to the prosthetic trunk and shunts blood into and/or through a branch vessel.

Some embodiments of the endovascular prosthetic system of the present invention comprise a prosthetic device comprising structural support. In some embodiments this structural support is a stent. In one embodiment, the stent may be formed by a plurality of discontinuous stent elements. In another embodiment, the stent may be formed from a single stent element. The stent may be located on the exterior of the device, the interior of the device, or both. The stent may be balloon-expandable or a self-expanding stent. Typically, the stent has a circular cross-section when fully expanded so as to conform to the generally circular cross-section of a body lumen. In one example, the stent may comprise struts and acute bends or apices that are arranged in a zig-zag configuration in which the struts are set at angles to each other and are connected by the acute bends. The present invention can be used with a wide variety of stent configurations, including, but not limited to, shape memory alloy stents, expandable stents, and stents formed in situ.

Preferably, the stent is formed from nitinol, stainless steel, tantalum, titanium, gold, platinum, inconel, iridium, silver, tungsten, cobalt, chromium, or another biocompatible metal, or alloys of any of these. Examples of other materials that may be used to form stents include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid, or copolymers thereof; a polyanhydride, polycaprolactone, polyhydroxybutyrate valerate, or another biodegradable polymer, or mixtures or copolymers of these; a protein, an extracellular matrix component, collagen, fibrin, or another biologic agent; or a suitable mixture of any of these. Preferably, the stent is a nitinol or stainless steel stent.

The term "stent graft" refers to a type of endoluminal device made of a tubular graft material and supported by at least one stent.

The stent graft material is preferably made of woven polyester having a twill weave and a porosity of about 350 ml/min/cm2 (available from Vascutek® Ltd., Renfrewshire, Scotland, UK). The stent graft material is preferably made of seamless woven polyester. The prosthetic trunk and stent graft material can also be made of any other at least substantially biocompatible material, including such fabrics as other polyester fabrics, polytetrafluoroethylene (PTFE), expanded PTFE, and other synthetic materials known to those of skill in the art. Naturally occurring biomaterials, such as collagen, are also highly desirable, particularly a derived collagen material known as extracellular matrix (ECM), such as small intestinal submucosa (SIS). Other examples of ECMs are pericardium, stomach submucosa, liver basement membrane, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr; U.S. Pat. No. 6,206,931 to Cook et al.; U.S. Pat. No. 6,358,284 to Fearnot et al.; 17 Nature Biotechnology 1083 (November 1999); and WIPO Publication WO 98/22158 of May 28, 1998, to Cook et al., which is the published application of PCT/US97/14855. All of these references are incorporated herein by reference. It is also preferable that the material is non-porous so that it does not leak or sweat under physiologic forces.

Graft materials may also include porous polymer sheet of a biocompatible material. Examples of biocompatible polymers from which porous sheets can be formed include polyesters, such as poly(ethylene terephthalate), polylactide, polyglycolide, and copolymers thereof; fluorinated polymers, such as polytetrafluoroethylene (PTFE), expanded PTFE (ePTFE) and poly(vinylidene fluoride); polysiloxanes, including polydimethyl siloxane; and polyurethanes, including polyetherurethanes, polyurethane ureas, polyetherurethane ureas, polyurethanes containing carbonate linkages, and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids, and polysulfones, in addition to polyesters, fluorinated polymers, polysiloxanes, and polyurethanes as listed above. Preferably the porous sheet is made of one or more polymers that do not require treatment or modification to be biocompatible. More preferably, the porous sheet includes a biocompatible polyurethane. Examples of biocompatible polyurethanes include Thoralon® (Thoratec, Pleasanton, Calif.), Biospan®, Bionate®, Elasthane®, Pursil® And Carbosil® (Polymer Technology Group, Berkeley, Calif.).

Preferably the porous polymeric sheet contains the polyurethane Thoralon®. As described in U.S. Patent Application Publication No. 2002/0065552 A1, incorporated herein by reference, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (Thoratec) is a segmented polyether urethane urea containing a soft segment and a hard segment. The soft segment is made of polytetramethylene oxide (PTMO) and the hard segment is made from the reaction of 4,4'-diphenylmethane diisocyanate (MDI) and ethylene diamine (ED). The SMA-300 component (Thoratec) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A porous polymeric sheet can be formed from these two components by dissolving the base polymer and additive in a solvent such as dimethylacetamide (DMAC) and solidifying the mixture by solvent casting, or by coagulation, in a liquid that is a non-solvent for the base polymer and additive.

Thoralon® has been used in certain vascular applications and is characterized by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® is useful in larger vessels, such as the abdominal aorta, where elasticity and compliance is beneficial.

In addition to Thoralon®, other polyurethane ureas may be used as a porous sheet. For example, the BPS-215 component with a MDI/PTMO mole ratio ranging from about 1.0 to about 2.5 may be used. Such polyurethane ureas preferably include a soft segment and a hard segment formed from a diisocyanate and diamine. For example, polyurethane ureas with soft segments such as polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic, or a mixture of aliphatic and aromatic moieties. Examples of diisocyanates include tetramethylene diisocyanate, hexamethylene diisocyanate, trimethylhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate, and mixtures thereof.

The diamine used as a component of the hard segment includes aliphatic amines, aromatic amines, and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

In addition to polyurethane ureas, other polyurethanes, preferably those having a chain extended with diols, may be used as a porous sheet. Polyurethanes modified with cationic, anionic, and aliphatic side chains may also be used. See, for example, U.S. Pat. No. 5,017,664. Polyurethanes may need to be dissolved in solvents such as dimethyl formamide, tetrahydrofuran, dimethyacetamide, dimethyl sulfoxide, or mixtures thereof.

The soft segments of these polyurethanes may contain any of the soft segments mentioned above, such as polytetramethylene oxide, polyethylene oxide, polypropylene oxide, polycarbonate, polyolefin, polysiloxane (i.e., polydimethylsiloxane), other polyether soft segments made from higher homologous series of diols, and mixtures of these soft segments. The soft segments may have amine end groups or alcohol end groups.

The hard segment may be formed from any of the diisocyanates listed above, such as 4,4'-diphenylmethane diisocyanate, tetramethylene diisocyanate, hexamethylene diisocyanate, trimethylhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate, and mixtures thereof.

The hard segment may be formed from one or more polyols. Polyols may be aliphatic, aromatic, cycloaliphatic, or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

In addition, the polyurethanes may also be end-capped with surface active end groups, such as, for example, polydimethylsiloxane, fluoropolymers, polyolefin, polyethylene oxide, or other suitable groups. See, for example, the surface active end groups disclosed in U.S. Pat. No. 5,589,563, which is incorporated herein by reference.

The porous polymeric sheet may contain a polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as Elast-Eon 2® and Elast-Eon 3® (Aortech Biomaterials, Victoria, Australia); polytetramethyleneoxide (PTMO) and polydimethylsiloxane (PDMS) polyether-based aromatic siloxane-polyurethanes such as Pursil®-10, -20, and -40 TSPU; PTMO and PDMS polyether-based aliphatic siloxane-polyurethanes such as Pursil AL-5® and AL-10 TSPU®; aliphatic, hydroxy-terminated polycarbonate and PDMS polycarbonate-based siloxane-polyurethanes such as Carbosil®-10, -20, and -40 TSPU (all available from Polymer Technology Group). The Pursil®, Pursil-AL®, and Carbosil® polymers are thermoplastic elastomer urethane copolymers containing siloxane in the soft segment, and the percent siloxane in the copolymer is referred to in the grade name. For example, Pursil-10® contains 10% siloxane. These polymers are synthesized through a multi-step bulk synthesis in which PDMS is incorporated into the polymer soft segment with PTMO (Pursil®) or an aliphatic hydroxy-terminated polycarbonate (Carbosil®). The hard segment consists of the reaction product of an aromatic diisocyanate, MDI, with a low molecular weight glycol chain extender. In the case of Pursil-AL® the hard segment is synthesized from an aliphatic diisocyanate. The polymer chains are then terminated with a siloxane or other surface modifying end group. Siloxane-polyurethanes typically have a relatively low glass transition temperature which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Patent Application Publication No. 2002/0187288 A1, which is incorporated herein by reference.

The porous polymer sheet may contain polytetrafluoroethylene or expanded polytetrafluoroethylene (ePTFE). Films or sheets of ePTFE are typically porous without the need for further processing. The structure of ePTFE can be characterized as containing nodes connected by fibrils. Porous ePTFE can be formed, for example, by blending PTFE with an organic lubricant and compressing it under relatively low pressure. Using a ram type extruder, the compressed polymer is then extruded through a die, and the lubricant is removed from the extruded polymer by drying or other extraction method. The dried material is then rapidly stretched and/or expanded at elevated temperatures. This process can provide for ePTFE having a microstructure characterized by elongated nodes interconnected by fibrils. Typically, the nodes are oriented with their elongated axis perpendicular to the direction of stretch. After stretching, the porous polymer is sintered by heating it to a temperature above its crystalline melting point while maintaining the material in its stretched condition. This can be considered as an amorphous locking process for permanently setting the microstructure in its expanded or stretched configuration. The structure and porosity of ePTFE is disclosed, for example, in U.S. Pat. Nos. 6,547,815 B2; 5,980,799; and 3,953,566; all of which are incorporated herein by reference. Structures of porous hollow fibers can be formed from PTFE, and these porous hollow fibers can be assembled to provide a cohesive porous sheet. Porous hollow fibers containing PTFE are disclosed, for example, in U.S. Pat. No. 5,024,671, which is incorporated herein by reference.

Polymers can be processed to be porous sheets using standard processing methods, including solvent-based processes such as casting, spraying and dipping, and melt extrusion processes. Extractable pore forming agents can be used during processing to produce porous sheets. Examples of extractable pore forming agents include inorganic salts such as potassium chloride (KCl) and sodium chloride (NaCl), organic salts, and polymers such as poly(ethylene glycol) (PEG) and polyvinylpyrrolidone (PVP). Pore forming agents may have a particle size from about 10 μm to about 500 μm, from about 20 μm to about 100 μm, and from about 10 μm to about 40 μm. The amount of pore forming agent relative to the polymer may be from about 20 percent by weight (wt %) to about 90 wt %, and from about 40 wt % to about 70 wt %. These sizes and amounts of pore forming agents can provide for a high degree of porosity following extraction of the pore forming agent. The porosity can be from about 20 wt % to about 90 wt % and from about 40 wt % to about 70 wt % of the final product.

Porous sheets may be in the form of a microporous, open-celled structure in which the pores are substantially interconnected. Microporous structures can be formed by extrusion of a mixture of polymer and one or more blowing agents. Microcellular polymeric foams can be produced by exposing the polymer to super-critical $CO_2$ under high temperature and pressure to saturate the polymer with the super-critical $CO_2$, and then cooling the polymer. Microcellular foams can be produced as described, for example, in U.S. Pat. Nos. 4,473,665 and 5,160,674, which are incorporated herein by reference. The foaming process can be carried out on extruded polymer tube by first dissolving an inert gas such as nitrogen or $CO_2$ under pressure into the polymer, and then forming microvoids by quickly decreasing the solubility of the gas in the polymer by changing the pressure or temperature, thus inducing thermodynamic instability. Examples of microporous polymeric structures are disclosed, for example, in U.S. Pat. No. 6,702,849 B1, which is incorporated herein by reference.

Porous Thoralon® can be formed by mixing the polyetherurethane urea, the surface modifying additive and a particulate substance in a solvent. Preferably the particulate is insoluble in the solvent, and the particulate may be any of a variety of different particulates or pore forming agents. For example, the solvent may be DMAC, and the particulate may be an inorganic salt. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting void-to-volume ratio can be substantially equal to the ratio of salt volume to the volume of the polymer plus the salt. The resulting pore diameter can also be substantially equal to the diameter of the salt grains.

The present invention provides an endovascular prosthetic device that can be used as a part of a system for treating a vasculature. The device comprises a primary prosthesis comprising major lumen. There is also a socket that has at least a portion that extends into the major lumen and that portion is angled in a proximal direction to direct blood flowing from the heart to the branch artery. The socket receives a secondary prosthesis that will be deployed in a branch artery. There is also a hole through a distal side of the socket to accommodate a guide wire that passes through the major lumen from a distal location into the socket and into the branch artery. The guide wire is configured to facilitate placement of the secondary prosthesis in the branch artery. In some embodiments, the prosthetic device can be implanted without a guide wire and the guide wire is then inserted manually once the prosthetic device is in place.

There are also embodiments for use in the aorta with fenestrations for secondary prostheses to be implanted in the renal or iliac arteries. Such embodiments also comprise pre-loaded guide wires.

Some embodiments provide a system for treating an aneurysm in the aortic arch. The system includes the endovascular prosthetic device as described above and also the secondary prosthesis for implantation in a branch artery. There are also embodiments wherein the primary prosthesis has at least one socket corresponding to a branch artery and at least one secondary prosthesis for implantation in a branch artery. Some embodiments comprise two sockets or three sockets with two or three secondary prostheses for implantation in branch arteries.

The endovascular prosthetic device is adapted for implantation in a constrained configuration and deployment to an expanded configuration. The guidewire is pre-loaded with the device to reduce the time usually taken to maneuver a guide wire through an aortic branch artery and through a socket angled in a proximal direction. The hole in the socket in the present invention is through the distal side of that portion of the socket extending into the major lumen. The guide wire extends through the major lumen, hole and socket while in the constrained and expanded configuration.

Turning to FIG. 1A, a prosthetic device is illustrated with a primary prosthesis 10 comprising a major lumen 12 extending therethrough from the proximal end 3 to the distal end 5 of the primary prosthesis 10. The major wall 14 contains the major lumen 12 and occludes an aneurysm once deployed. First 31, second 16, and third 19 openings are shown in the major wall 14 that correspond to the first 40, second 18, and third 20 sockets and to three branch arteries that branch away from the vessel in which the primary prosthesis 10 is deployed. Although the embodiment illustrated has three sockets, other embodiments of the present invention provide primary prostheses with one or two openings corresponding to one or two sockets. In other embodiments, there is at least one socket in the major wall 14. There are also embodiments wherein the primary prosthesis 10 further comprises a structural support around at least a portion of the major wall 14. The structural support can be a stent in some embodiments.

At least a portion of the first 40, second 18, and third 20 sockets extend into the major lumen 12 from the openings 31, 16, and 19. While the first 40 and second 18 sockets are angled in a proximal direction, the third 19 socket is angled in a distal direction in the figure shown. The sockets, therefore, are arranged in fluid communication with the major lumen 12. There may be other embodiments in which the sockets are angled in directions suitable for other specified treatments. The first 40, second 18, and third 20 sockets mate with the proximal ends of secondary prostheses to form a secure seal with the primary prosthesis 10 at the openings. The sockets 40, 18, and 20 are angled to receive the flow of blood and direct it through their minor lumens 11 into the branch arteries. The sockets 40, 18, and 20 are further designed to be hemodynamically effective and to minimize blood turbulence in the primary prosthesis 10. As such the sockets can have an internal helical design as described in U.S. Patent Publication No. 2006/0247761, incorporated by reference herein in its entirety. Also, the sockets can have baffles straddling either side of the socket to direct blood flow around sections of the internal helical socket that may cause turbulent blood flow. The sockets have fenestrations 15 that are in fluid communication with the minor lumens 11 and the major lumen 12. The fenestrations 15 are located in the distal sides 5 of the minor walls 13 of the sockets, the portion that extends into the major lumen. Although FIG. 1 illustrates an embodiment with three sockets 40, 18, and 20, there are other embodiments comprising at least one socket or two sockets. In the embodiment illustrated, there is a first socket 40 and opening 31 configured to direct blood flow into the innominate artery. The second socket 18 and opening 16 are configured to direct blood flow into the left common carotid artery. The third socket 20 and opening 19 are configured to direct blood flow into the left subclavian artery.

Figure 1B:
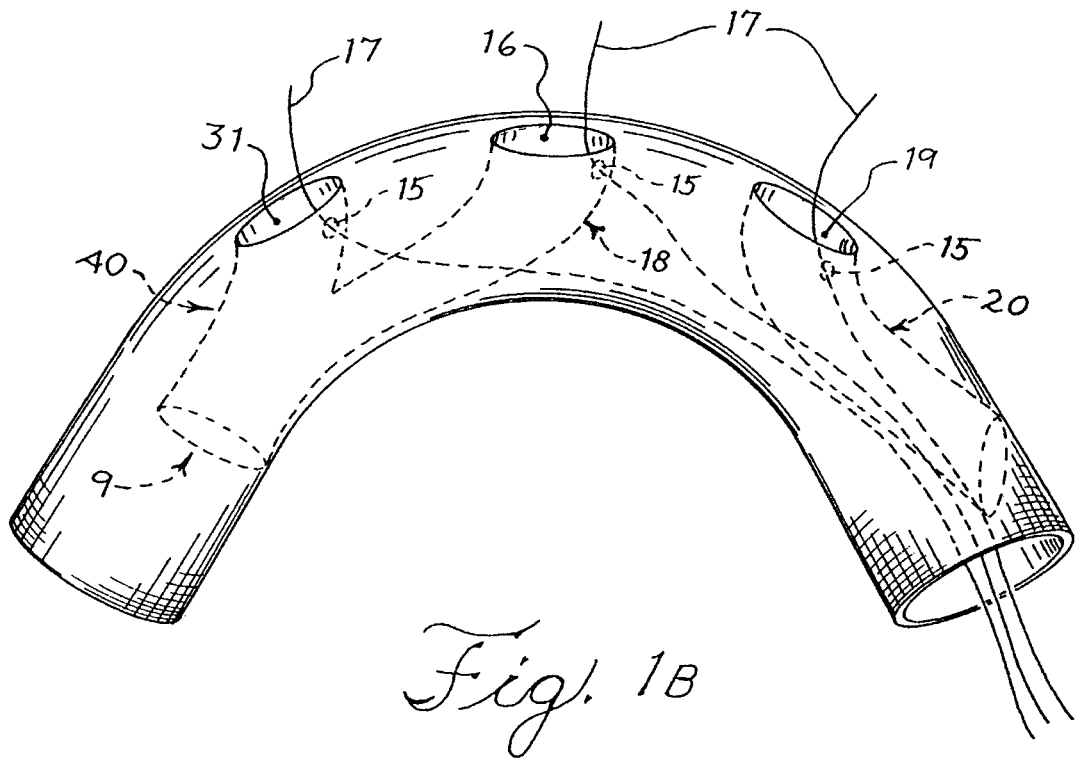
FIG. 1B is an illustration of a prosthetic device with the first and second sockets sharing a common anastomosis.
Figure 1C:
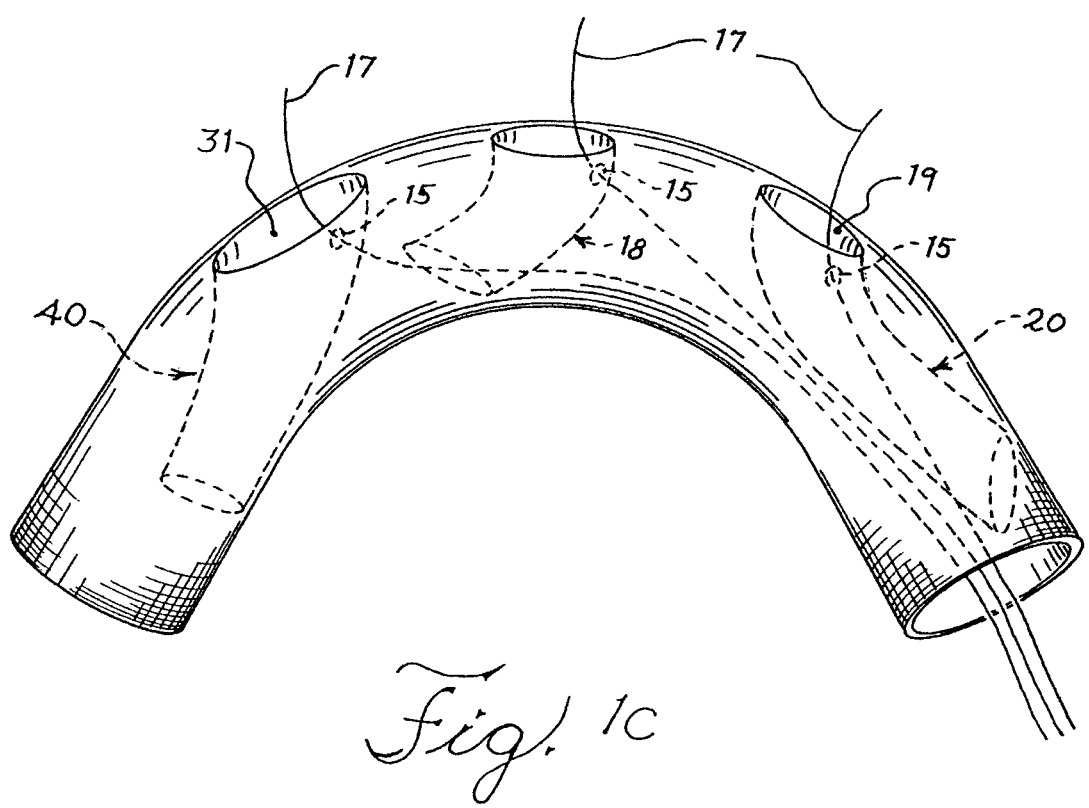
FIG. 1C is an illustration of a prosthetic device with branches having diameters that taper to a smaller size from the opening to the proximal portion of the branch.

The sockets may be bifurcated. FIG. 1B is an illustration of an embodiment where the first 40 and second 18 sockets share a common anastomosis. The sockets can also taper from a large diameter to a smaller diameter. In FIG. 1C, the diameter of the opening 31 of the first socket 40 is larger than the remainder of the branch. In some embodiments, the branches taper from a range of about 13 mm to 15 mm to a range of about 9 mm to 11 mm. In some embodiments, the branch tapers from about 14 mm to about 10 mm.

Guide wires 17 extend from the distal end 5 of the primary prosthesis 10 through the fenestrations 15 to extend into the minor lumens 11 of the sockets and out of the primary prosthesis 10 through the openings in the major wall 14. Because of their arrangement in the present invention, upon placement and deployment, the guide wires 17 will be positioned in the target vessels for snaring with a double lumen catheter or some other guide wire. The guide wires 17 can have angled tips, flexible tips, compliant tips, or blunt tips.

Figure 2A:
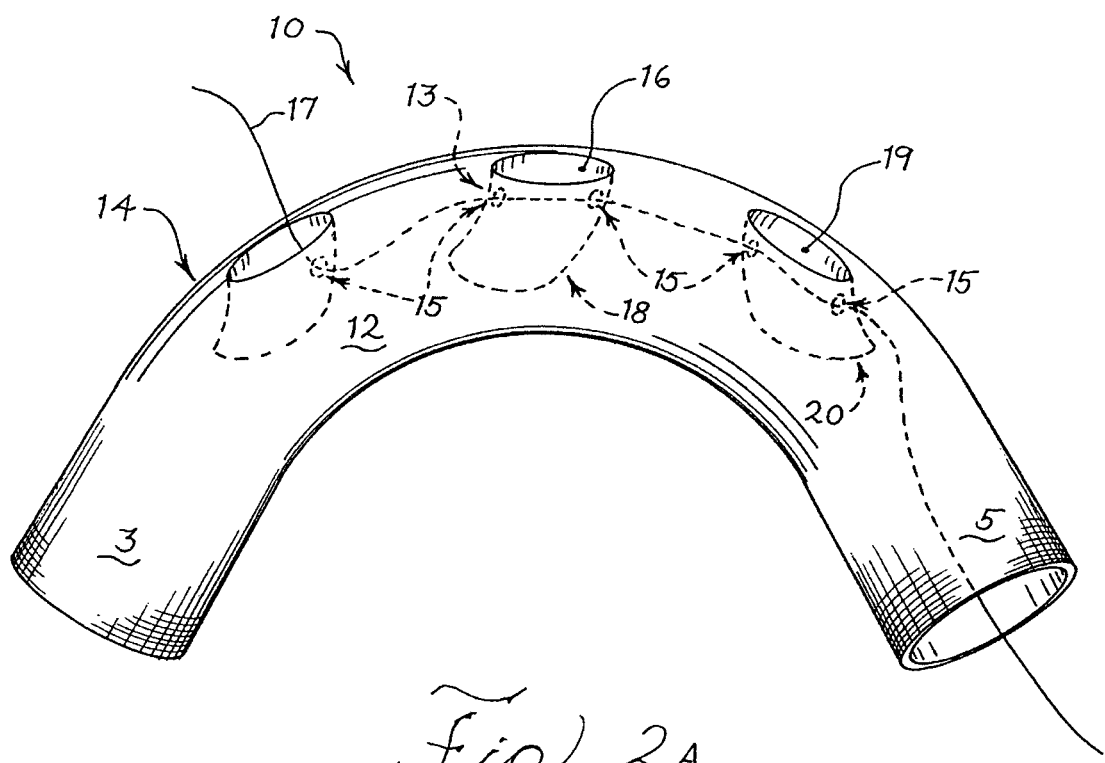
FIG. 2A is a schematic representation of a prosthetic device with two sockets and one guide wire that is threaded through the fenestrations in the wall of each socket.

FIG. 2A shows an embodiment having one guide wire 17 threaded through the fenestrations 15 of the first 40, second 18, and third 20 branches. Although the embodiment shown has two fenestrations 15 on the second 18 and third 20 branches, there are also embodiments having only one fenestration 15 per socket. The guide wire 17 is used to guide and deploy a secondary prosthesis, such as a side branch graft, into the first 31 opening of the first 40 socket. After deployment of the first secondary prosthesis, the guide wire 17 is pulled out of the first 40 socket and into the second 18 branch. In such an embodiment, the guide wire 17 tip preferably comprises nitinol or other shape memory alloy. This allows the guide wire 17 tip to assume an orientation pointing out of the second 16 opening.

Figure 2B:
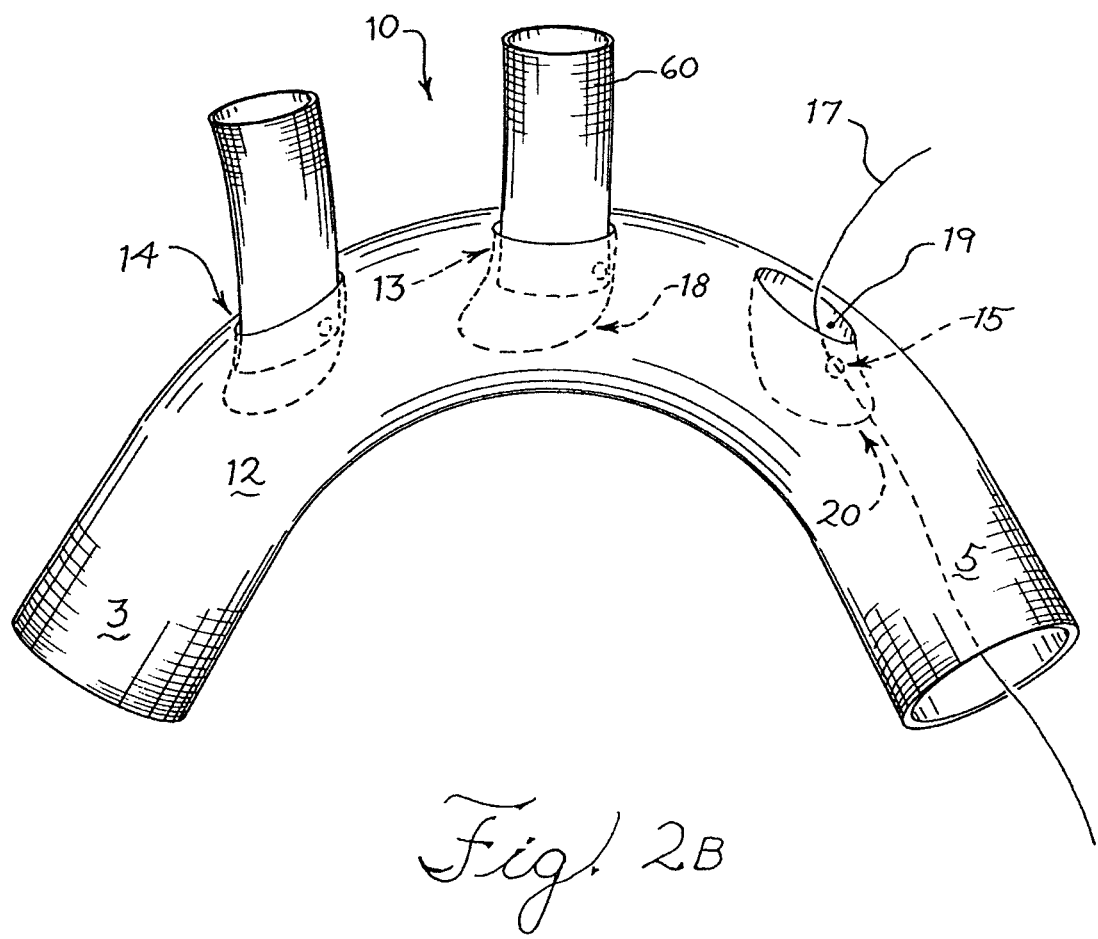
FIG. 2B illustrates the guide wire threaded though the second socket and corresponding hole.

As seen in FIG. 2B, the guide wire 17 has been pulled from the first socket 40 and the second socket 18 and into the third 20 socket. This may be done after the guide wire has been used to deploy a secondary prosthesis in the second socket 18. As the guide wire 17 tip retains its shape, it points out of the third opening 19 just as it pointed out of the first opening 16. The guide wire 17 can now be used to place a secondary prosthesis into the third socket 20.

The fenestrations 15 in the branches do not hinder blood flow once the prosthesis 10 is properly deployed. Once a secondary prosthesis, usually a tubular prosthesis such as a side branch graft, is positioned and deployed in a socket, the guide wire 17 is retracted from the fenestration 15. The proximal end of the secondary prosthesis occludes the fenestration 15 such that blood flow is not detrimentally affected.

Figure 3:
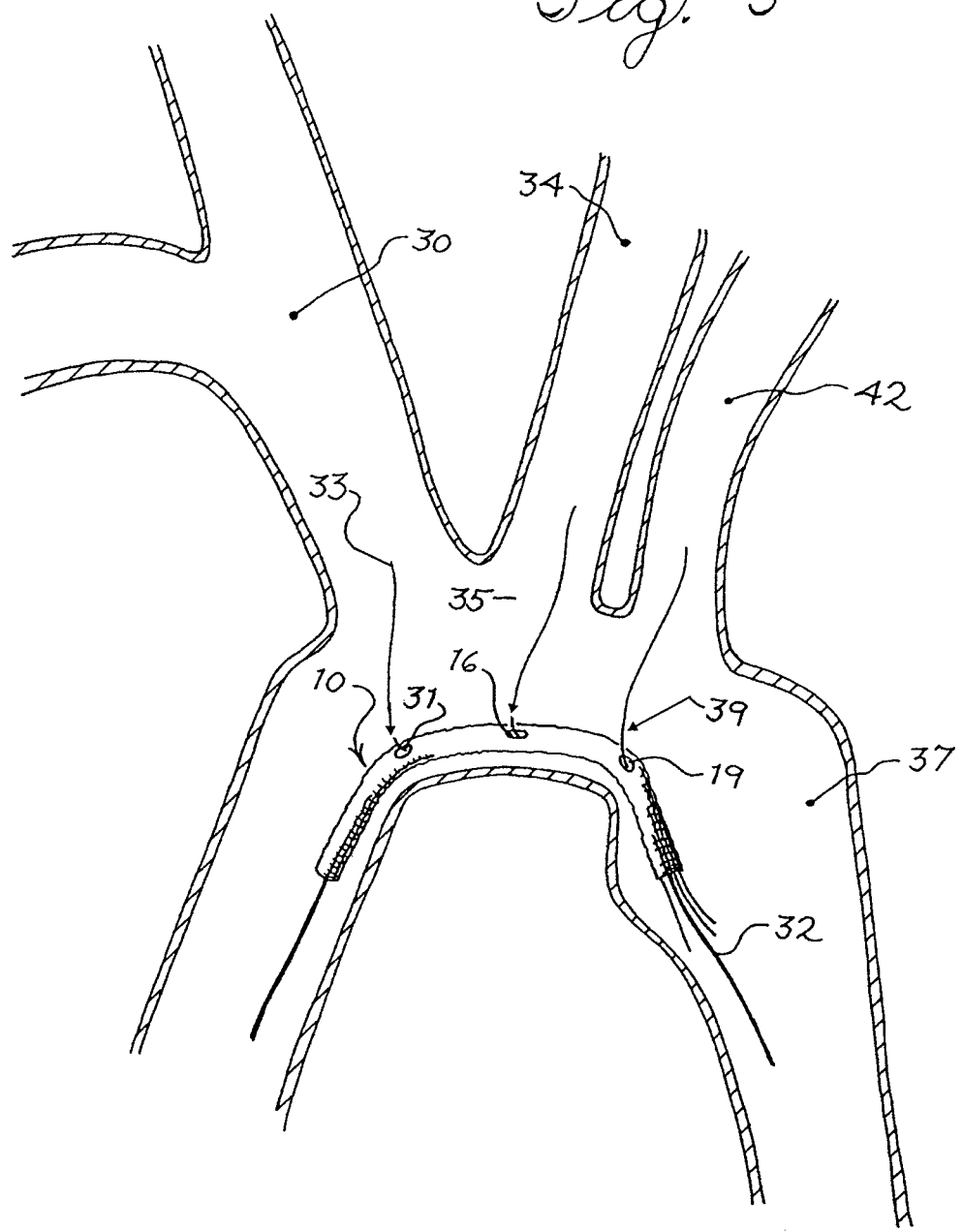
FIG. 3 is an illustration of a compacted prosthetic device in a large aneurysm of the aortic arch.

The device of the present invention can be deployed into the aortic arch by methods known in the art. FIG. 3 illustrates the system of the present invention with a primary prosthesis 10 being introduced into an aortic arch having a descending aneurysm 37. A main guide wire 32 is inserted into the femoral artery (right or left) through an incision and is guided through the descending aorta, the aortic arch, and the ascending aorta. The main guide wire 32 is guided to the aortic valve of the heart in some methods. The guide wires, now individually labeled 33, 35, and 39, are seen poking out of the three openings 31, 16, and 19.

Figure 4:
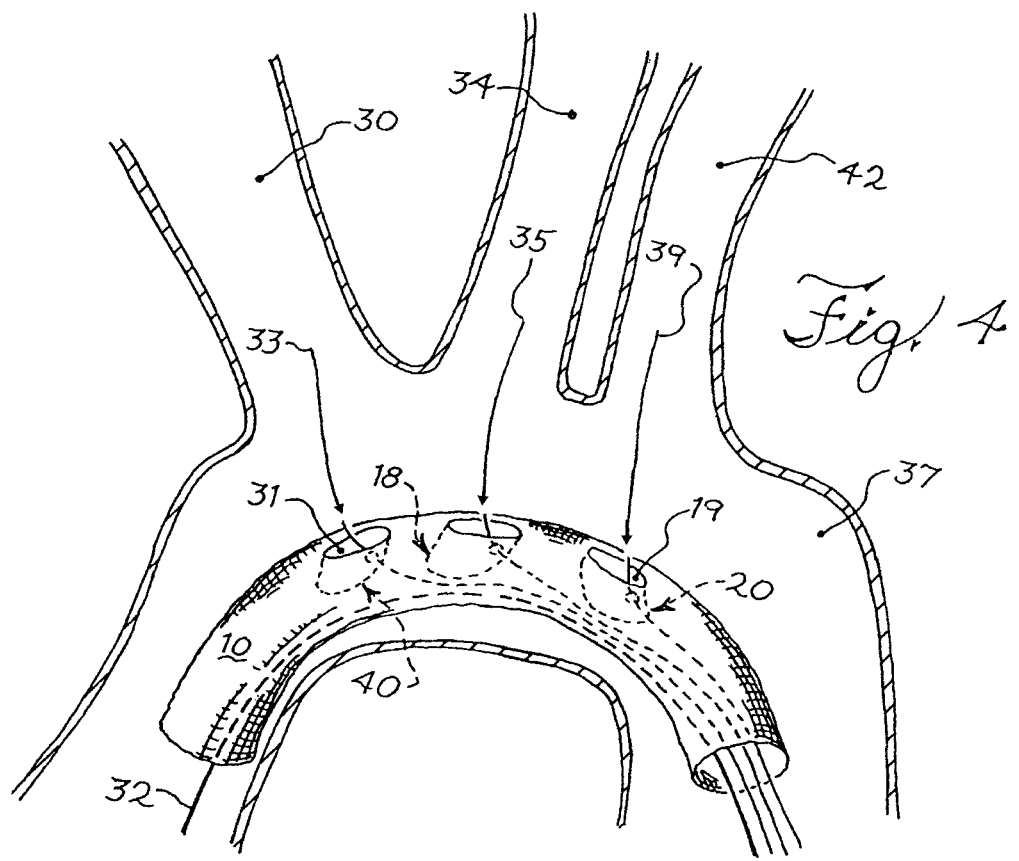
FIG. 4 is a schematic drawing of the prosthetic device in a semi-deployed configuration.

In FIG. 4, the primary prosthesis 10 is partially expanded. Although not shown, this can be accomplished with ties partially constraining the prosthesis. Holes 31, 16, and 19 are aligned with the innominate 30, left common carotid 34, and left subclavian 42 arteries, respectively. The guide wires 33, 35, and 39 are appropriately positioned in the arteries 30, 34, and 42 for snaring. Diagnostic imaging can be used to confirm the proper placement of all the elements. Radiopaque markers can be placed to mark the positions of the first 31, second 16, and third 19 openings. Radiopaque markers can also be placed at other locations on the primary prosthesis 10 to assist in marking the position of the implant. For instance, in some embodiments the radiopaque markers can be placed on the proximal 3 and distal 5 ends of the primary prosthesis 10.

Figure 5:
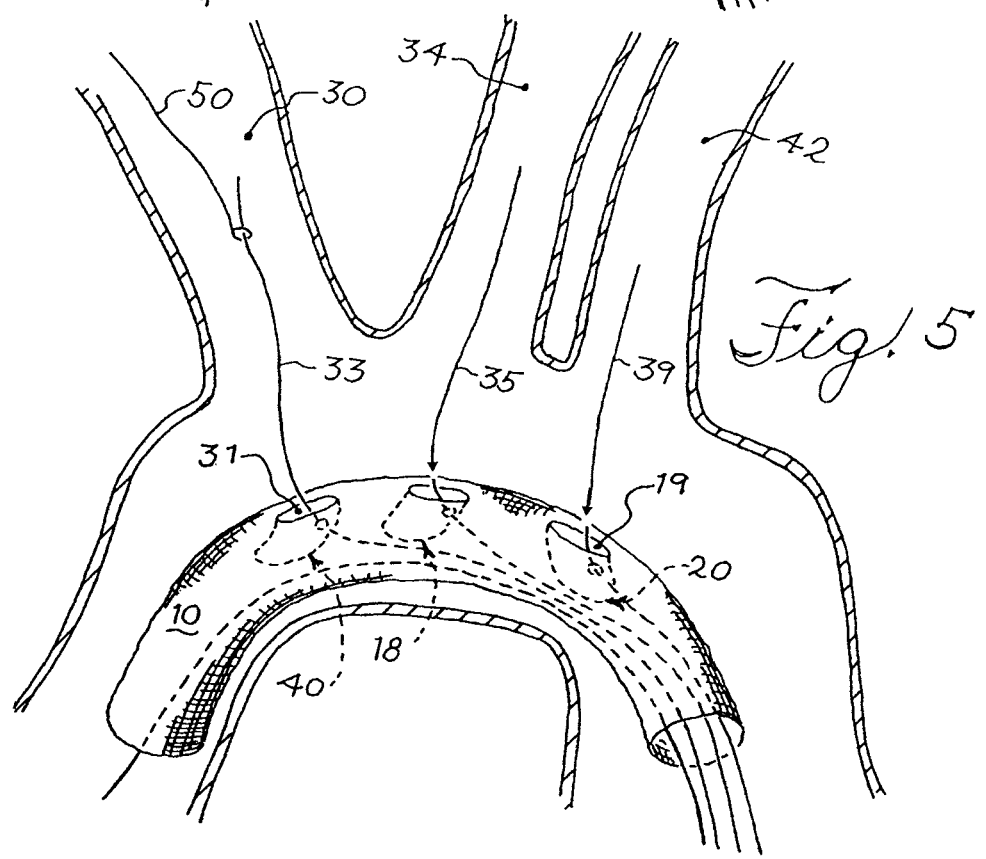
FIG. 5 is an illustration of a guide wire being snared in the innominate artery.
Figure 6:
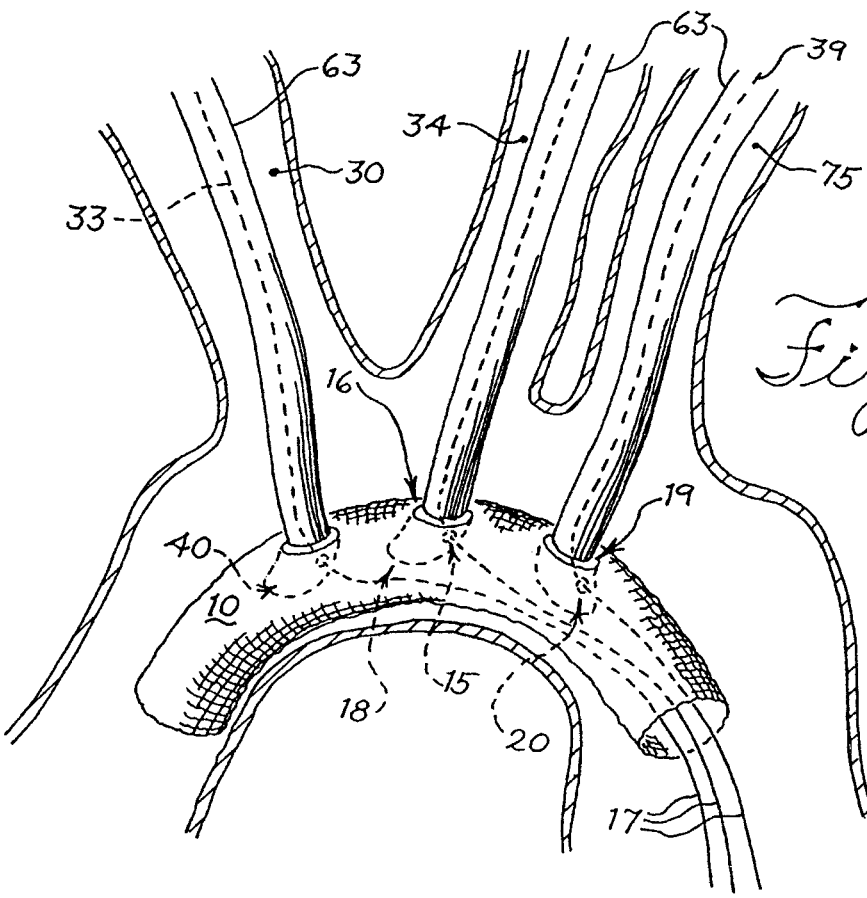
FIG. 6 is a schematic representation of sheaths placed into the sockets over their respective guide wires.
Figure 7:
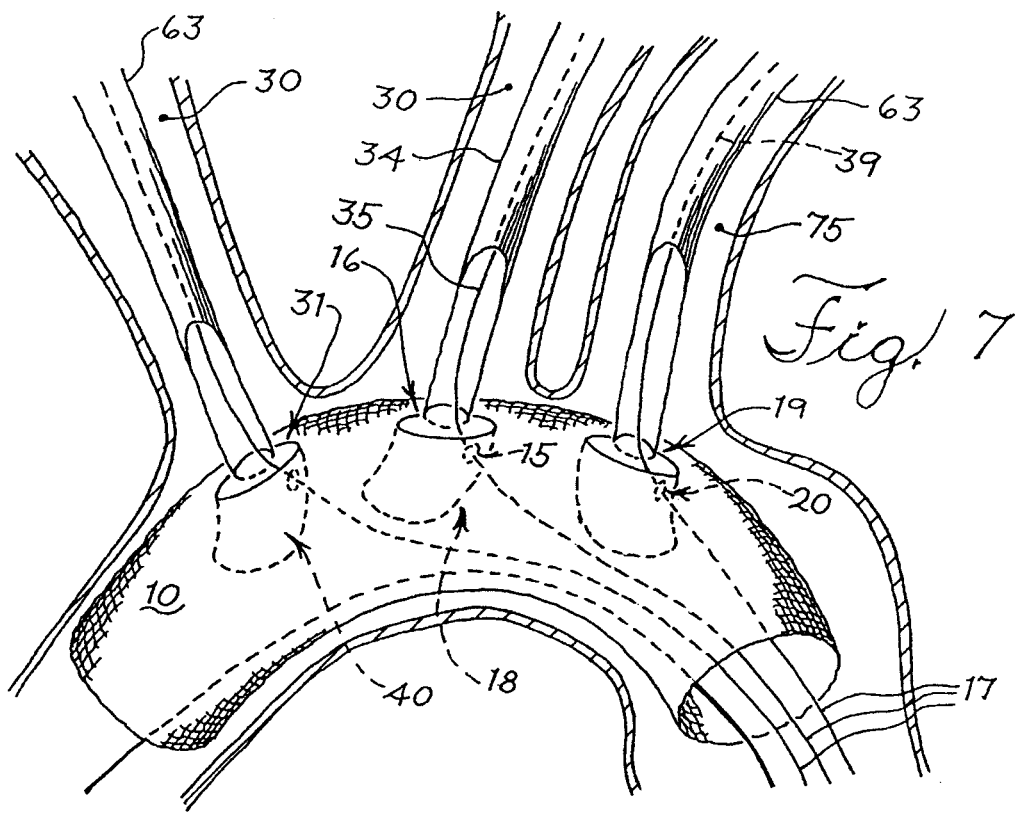
FIG. 7 illustrates second guide wires being placed into the prosthetic device through the sheaths.
Figure 8:
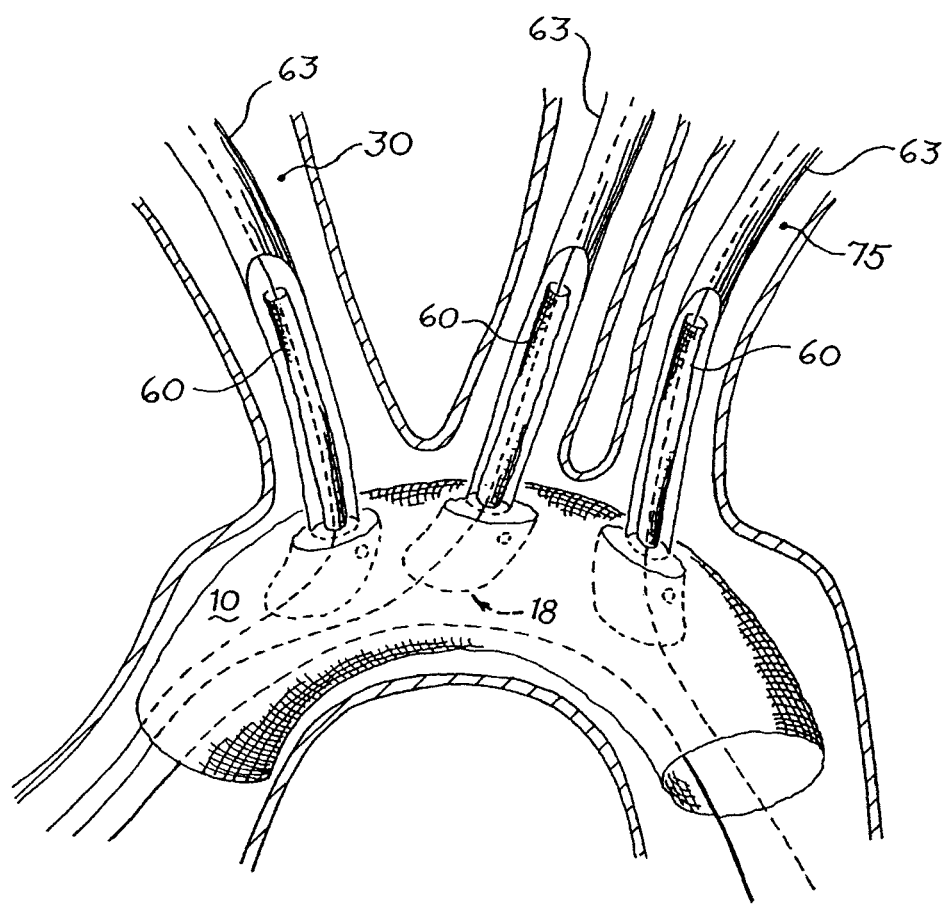
FIG. 8 is an illustration of secondary prostheses being implanted into the sockets through their respective sheaths.

Guide wire 33 projects into the innominate 30 artery where the guide wire 33 is captured by a snare 50 as shown in FIG. 5. Once snared, the surgeon uses the snare 50 to pull guide wire 33 through the innominate 30 artery toward the snare's 50 entry point. As illustrated in FIG. 6, a sheath 63 is then placed over the guide wire 33 and advanced through the innominate 30 artery to the opening 31. This sheath 63 is used to advance another guide wire 70 into the first socket 40 as shown in FIG. 7. Snares are used to capture the remaining guide wires 35 and 39 so that one or more sheaths 63 are advanced into the remaining openings 16 and 19. In the embodiment illustrated, the sheaths 63 are advanced to openings 16 and 19 in the second 18 and third 20 sockets while the primary prosthesis 10 is still partially constrained. Once the sheaths 63 have been advanced to their respective openings, the primary prosthesis 10 is fully expanded, as shown in FIG. 8. The primary prosthesis 10 can be expanded using means known in the art including, but not limited to, balloon expansion or by the loosening of constraining wire.

Figure 9:
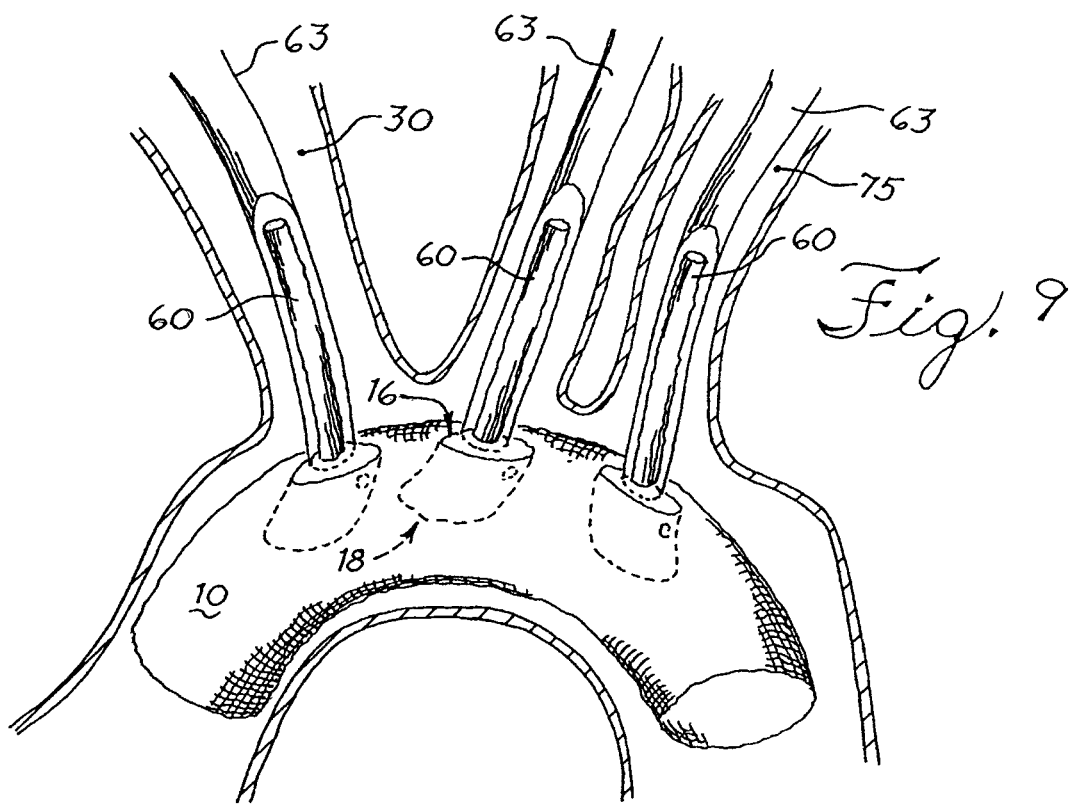
FIG. 9 is a view of the side branch stents in the prosthetic device without the second guide wires.
Figure 10:
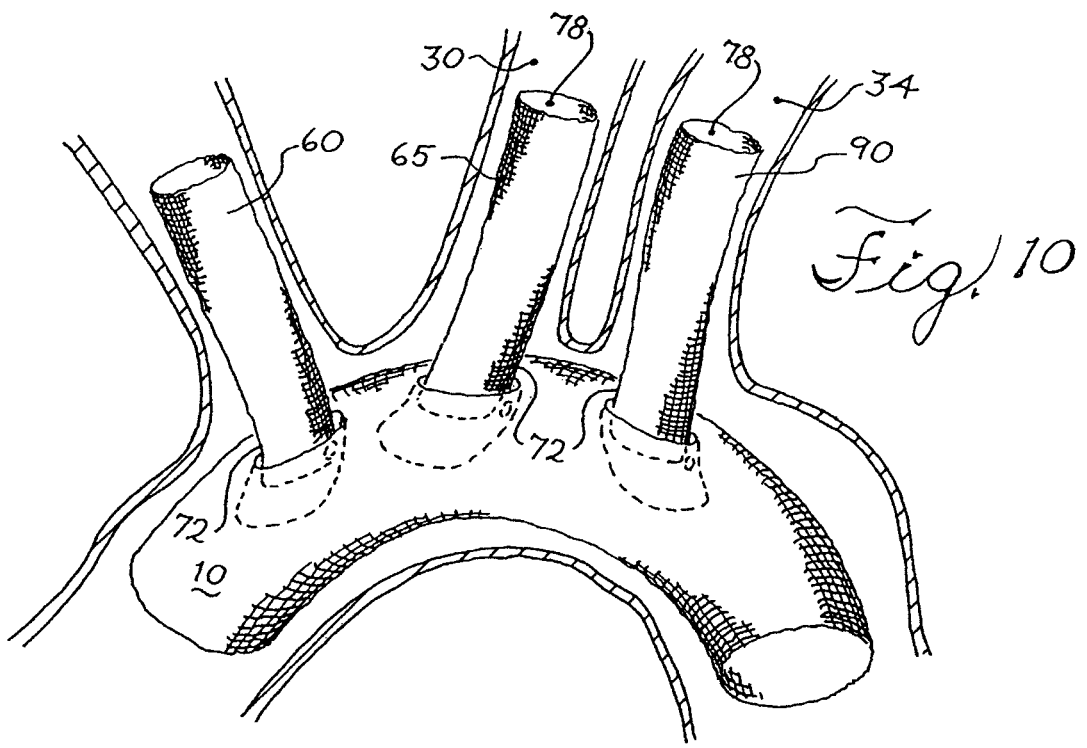
FIG. 10 is an illustration of the secondary prostheses in their fully expanded configuration.

Over guide wire 70, a secondary prosthesis 60 is advanced to the opening 31 of the first socket 40. In such embodiments, the prosthetic systems of the present invention further comprise at least one secondary prosthesis 60 having a proximal end 72 and a distal end with a lumen therethrough, the proximal end 72 being sealingly engaged with at least one socket in the major wall 14 and the distal end extending into the lumen of a branch artery. The secondary prosthesis 60 is a side branch graft in some embodiments and comprises a stent in many embodiments. FIG. 9 illustrates the system with the sheaths 63 removed. The proximal end 72 of the secondary prosthesis 60 is placed within the socket 40, as shown in FIG. 10, such that the fenestration 15 will be occluded by the secondary prosthesis 60 once it is expanded. The secondary prosthesis 60 is then expanded to substantially occupy the minor lumen 11 of the first socket 40 and the innominate artery 30.

The secondary prosthesis 60 may also be implanted using other methods known in the art. The secondary prosthesis 60 can be self expanding or expanded by balloon catheter and deployed such that the proximal end 72 is sealingly engaged with the opening 16. FIG. 9 illustrates other secondary prostheses 60 placed within the remaining sockets 18 and 20. FIG. 10 is an illustration of three secondary prostheses fully expanded in their respective sockets.

There are also embodiments of the prosthetic systems disclosed that comprise an prosthetic device comprising two sockets extending into the major lumen from corresponding holes and arranged in fluid communication with the major lumen. In such embodiments, the two sockets may correspond to any two of the innominate, left common carotid, or left subclavian arteries. Two secondary prostheses would also accompany this embodiment for placement in the two sockets. The system further comprises two guide wires, one for each socket. In some embodiments, there is one guide wire that is threaded through the holes of each socket.

There is an endovascular prosthetic device comprising a primary prosthesis with a primary lumen; a major socket in the primary prosthesis having a major lumen at least a portion of which extends into the primary lumen and comprising at least one minor socket with a minor lumen at least partially within the major lumen; and a fenestration in the wall of the major socket to accommodate a guide wire passing through the major, minor, and primary lumens and being configured to facilitate placement of a secondary prosthesis in a branch artery. The minor socket and the major socket can share a common distal wall. In such instances, the fenestration can be located in the distal wall in direction communication of the minor lumen and primary lumen.

Figure 11A:
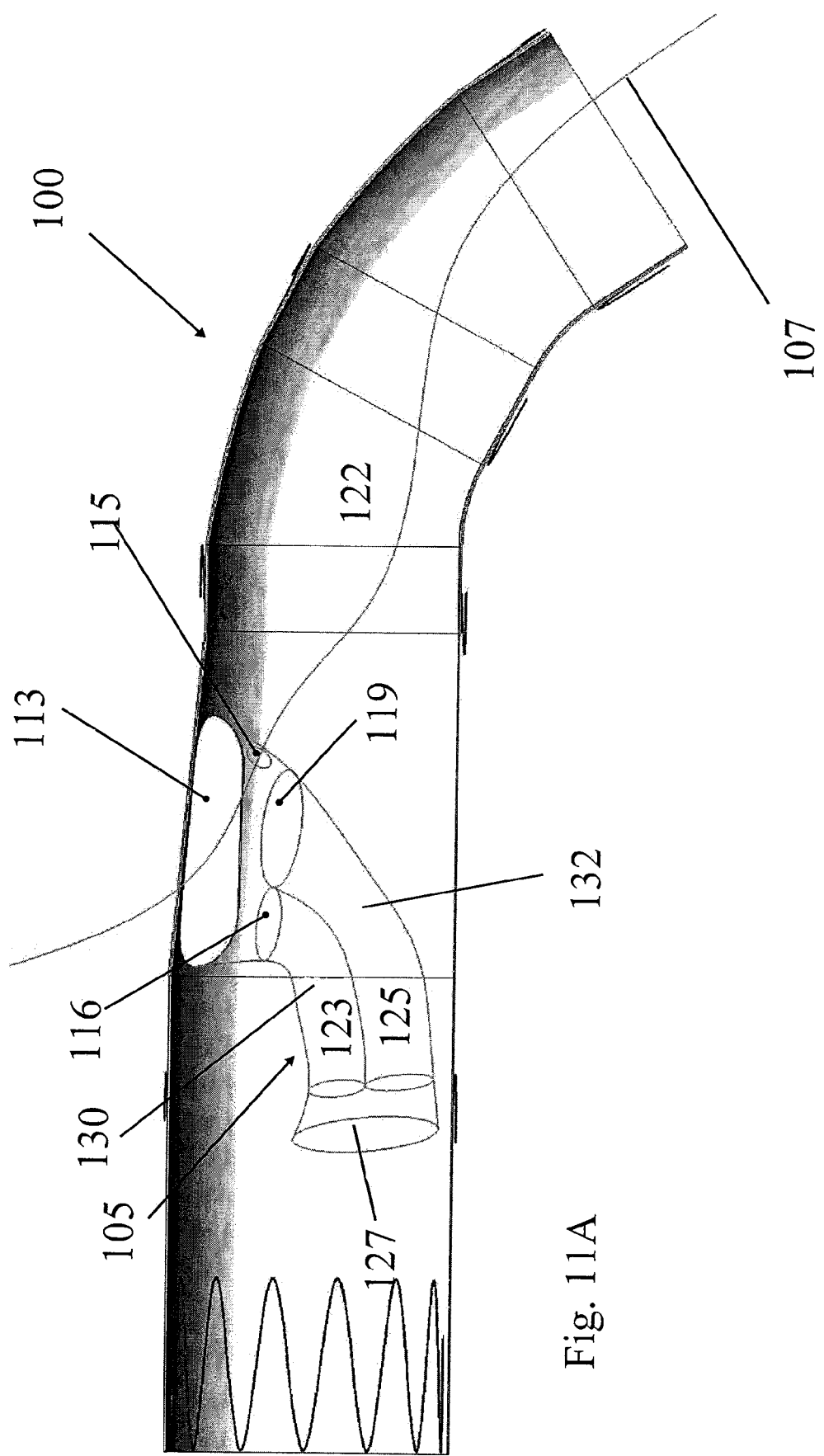
FIGS. 11A and 11B are side views of a prosthesis with a major socket containing two minor sockets.
Figure 11B:
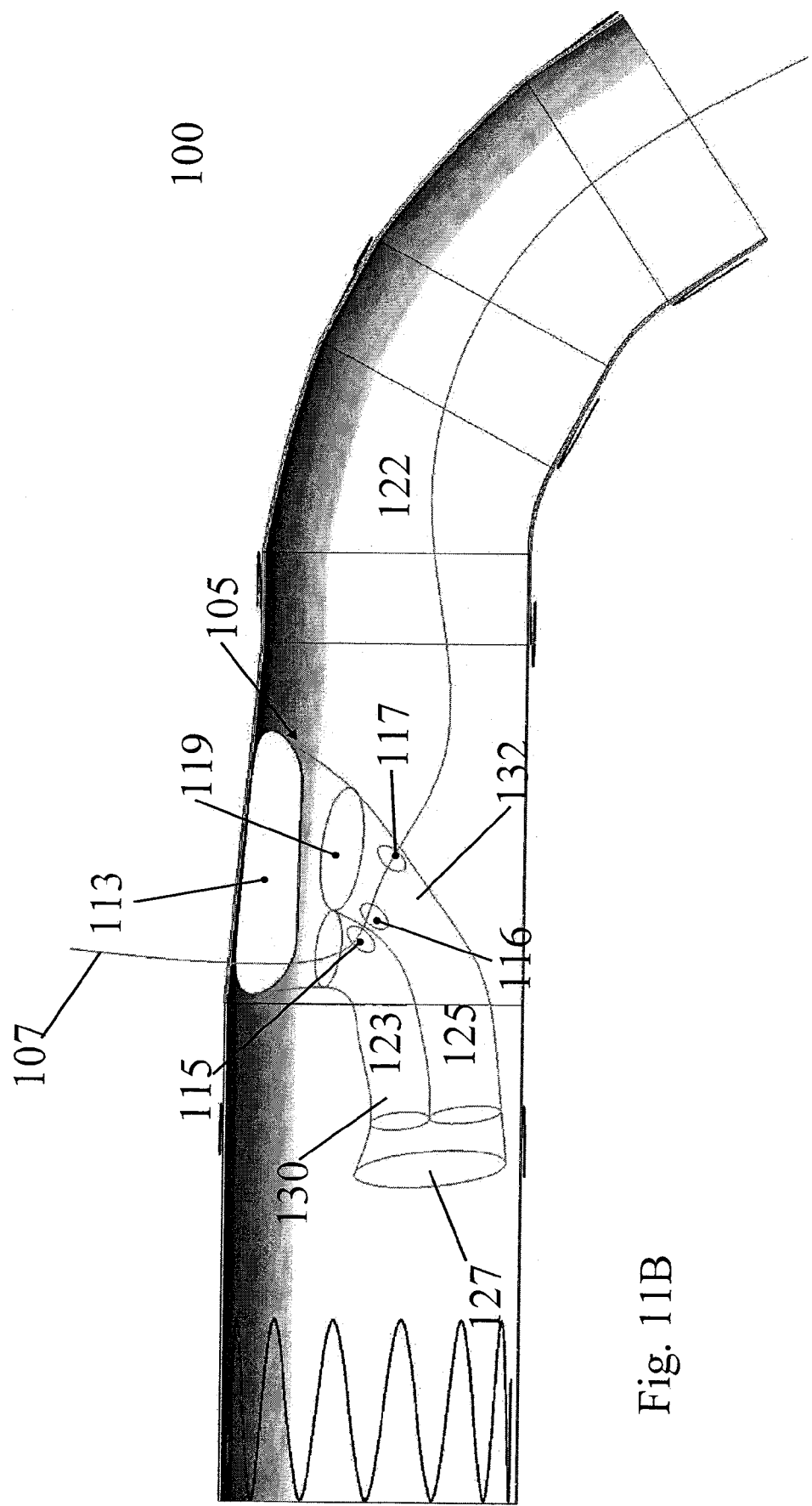

The prosthetic device can also have a socket that extends into the major lumen with a major opening 113 and at least one minor opening. In FIGS. 11A and 11B, the prosthetic device 100 has a socket 105 with one major opening 113 and two minor 116, 119 openings in the distal portion of the socket 105. Each minor opening 116, 119 corresponds to minor sockets 130, 132, respectively, that include minor lumens 123, 125, respectively, resting within the lumen 127 of the socket 105. The minor sockets can extend in the same direction as the lumen of the socket they rest within. In FIGS. 11A and 11B, the minor sockets 130, 132 extend in the same proximal direction as major lumen 127.

FIG. 11A shows one fenestration 115 in the distal side of the socket 105 just below the major opening 113 through which a guide wire 107 has been placed. In FIG. 11B, the guide wire 107 has been placed through three fenestrations: one fenestration 115 in the distal wall of minor socket 130 and two fenestrations 118, 117 in the proximal distal walls of minor socket 132. The distal wall of minor socket 132 forms a portion of the distal wall of the major socket 105. Fenestration 117 is just below the minor opening 119 and is in fluid communication with the primary lumen 122 of the prosthetic device 100 and minor lumen 125.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. An endovascular prosthesis delivery system for implanting a prosthetic device, the endovascular prosthetic delivery system comprising:
   a delivery catheter;
   a primary prosthesis disposed on the delivery catheter, the primary prosthesis comprising:
      a major lumen;
      a socket for receiving a secondary prosthesis, which secondary prosthesis is deployed in a branch artery, the socket having at least a portion that extends into the major lumen, said portion being angled in a proximal direction so as to direct blood flowing from the heart to the branch artery; and
      a fenestration in the wall of the socket sized to accommodate a preloaded guide wire;
      where the guidewire is preloaded directly within the major lumen of the primary prosthesis disposed on the delivery catheter prior to implantation and passes through the major lumen from a distal location, through the fenestration, and into the socket, said guide wire being configured to facilitate placement of the secondary prosthesis in the branch artery.

2. The endovascular prosthetic device of claim 1 configured for placement in the aortic arch comprising first and second sockets corresponding to the left common carotid and left subclavian arteries respectively.

3. The endovascular prosthetic device of claim 1 configured for placement in the aortic arch comprising first, second, and third sockets corresponding to the innominate, left common carotid, and left subclavian arteries respectively.

4. The endovascular prosthetic device of claim 1 comprising first and second sockets, the endovascular prosthetic device further comprising first and second guide wires wherein the first guide wire extends through the fenestration in the wall of the first socket and the second guide wire extends through the fenestration in the wall of the second socket.

5. The endovascular prosthetic device of claim 1 comprising first and second sockets, the guide wire extending through the fenestration in the wall of the first socket and through the fenestration in the wall of the second socket.

6. The endovascular prosthetic device of claim 1 wherein the endovascular prosthetic device comprises a first, second, and third sockets, the guide wire extending through the fenestration in the wall of the first socket, the fenestration in the wall of the second socket, and the fenestration in the wall of the third socket.

7. The endovascular prosthetic device of claim 1 wherein the device has first and second sockets for receiving first and second secondary prosthesis, wherein the proximal end of the first secondary prosthesis is sealingly engaged to the first socket and the proximal end of the second secondary prosthesis is sealingly engaged to the second socket.

8. An endovascular prosthetic system for implantation in a vessel, the system comprising:
   a primary prosthesis comprising a major lumen;
   a socket in the primary prosthesis for receiving a secondary prosthesis for deployment in a branch artery, the socket having at least a portion that extends into the major lumen, said portion being angled in a proximal direction so as to direct blood flowing from the heart to the branch artery; and
   a fenestration in the wall of the socket sized to accommodate a preloaded guide wire;
   where the guidewire is preloaded directly within the major lumen of the primary prosthesis passes through the major lumen from a distal location, through the fenestration, and into the socket, said guide wire being configured to facilitate placement of the secondary prosthesis in the branch artery.

9. The system of claim 8 wherein the primary prosthesis is configured for placement in the aortic arch comprising first and second sockets corresponding to the left common carotid and left subclavian arteries respectively.

10. The system of claim 8 wherein the primary prosthesis is configured for placement in the aortic arch comprising first, second, and third sockets corresponding to the innominate, left common carotid, and left subclavian arteries respectively.

11. The system of claim 8 wherein the primary prosthesis comprises first and second sockets, the system further comprising first and second guide wires wherein the first guide wire extends through the fenestration in the wall of the first socket and the second guide wire extends through the fenestration in the wall of the second socket.

12. The system of claim 8 wherein the primary prosthesis further comprises first and second sockets, the guide wire extending through the fenestration in the wall of the first socket and through the fenestration in the wall of the second socket.

13. The system of claim 8 wherein the primary prosthesis further comprises a first, second, and third sockets, the guide wire extending through the fenestration in the wall of the first socket, the fenestration in the wall of the second socket, and the fenestration in the wall of the third socket.

14. The system of claim 8 wherein the prosthetic device further comprises structural support around at least a portion of the major wall.

15. The system of claim 14 wherein the structural support is a stent.

16. An endovascular prosthetic device comprising:
   a primary prosthesis with a primary lumen;
   a major socket in the primary prosthesis comprising a major opening, a major lumen at least a portion of which extends into the primary lumen, and at least one minor socket with a minor opening and a minor lumen at least partially within the major lumen; and
   a fenestration in the wall of the major socket sized to accommodate a preloaded guide wire,
   where the guidewire is preloaded directly within the primary prosthesis and passes through at least the major and primary lumens and is configured to facilitate placement of a secondary prosthesis in a branch artery.

17. The endovascular prosthetic device of claim 16 comprising two minor sockets with each minor socket having a minor lumen.

18. The endovascular prosthetic device of claim 16 where the at least one minor socket shares a wall with the major socket and the fenestration is in direct fluid communication with the minor lumen of the minor socket.

19. The endovascular prosthetic device of claim 16 further comprising a guide wire that passes through a major or minor opening.

20. An endovascular prosthetic system for implanting an endovascular prosthetic device in a branching body vessel, the comprising:
   a tubular prosthesis having a proximal end, a distal end, a main lumen between the proximal and distal ends, a side wall, and at least one main lumen fenestration in the side wall of the tubular prosthesis;
   a socket disposed within the main lumen of the tubular prosthesis and having a first end in communication with the main lumen fenestration, a second end in communication with the main lumen, a minor lumen between the first and second ends, a socket sidewall, and a tubular socket fenestration disposed in the tubular socket sidewall between the first and second ends and providing communication between the main lumen and the minor lumen;
   a guide wire pre-loaded within the prosthesis without a separate catheter and directly disposed within the main lumen, and passing through the socket fenestration into the minor lumen.

* * * * *